United States Patent [19]
Fortier et al.

[11] Patent Number: 5,913,865
[45] Date of Patent: Jun. 22, 1999

[54] DISTAL END FOR LIGATING BAND DISPENSER

[75] Inventors: Richard C. Fortier, Concord; Liem T. Vu, Watertown, both of Mass.

[73] Assignee: Scimed Lifesystems, Inc., Maple Grove, Minn.

[21] Appl. No.: 09/079,925

[22] Filed: May 15, 1998

[51] Int. Cl.$^6$ ............................................. A61B 17/04
[52] U.S. Cl. .................................................. 606/140
[58] Field of Search ............................ 606/1, 135, 139, 606/165

[56] References Cited

U.S. PATENT DOCUMENTS

| | | | |
|---|---|---|---|
| 5,269,789 | 12/1993 | Chin et al. | 606/140 |
| 5,320,630 | 6/1994 | Ahmed | 606/140 |
| 5,356,416 | 10/1994 | Chu et al. | 606/140 |
| 5,398,844 | 3/1995 | Zaslavsky et al. | 221/208 |
| 5,423,834 | 6/1995 | Ahmed | 606/140 |
| 5,462,559 | 10/1995 | Ahmed | 606/140 |
| 5,507,797 | 4/1996 | Suzuki et al. | 606/140 |
| 5,569,268 | 10/1996 | Hosoda | 606/140 |
| 5,624,453 | 4/1997 | Ahmed | 606/140 |

*Primary Examiner*—Gary Jackson
*Attorney, Agent, or Firm*—Kenyon & Kenyon

[57] ABSTRACT

A supporting structure for a ligating band dispensing device adapted to be coupled to a distal end of an endoscope comprises a substantially cylindrical outer support surface adapted to receive a plurality of ligating bands thereon, wherein the support surface includes a channel extending therethrough from a distal end to a proximal end. The support surface further includes a plurality of shallow slots and deeper slots disposed on the distal end for retaining a trigger string. The shallow slots and deeper slots may be arranged in an alternating fashion, and each of the slots may be narrower than the trigger string to prevent the trigger string from prematurely exiting the slots. The support surface may also include a plurality of axially extending ridges to assist in deployment of the ligating bands by preventing the bands from sliding along the trigger line and facilitating rolling of the bands along the support surface.

41 Claims, 10 Drawing Sheets

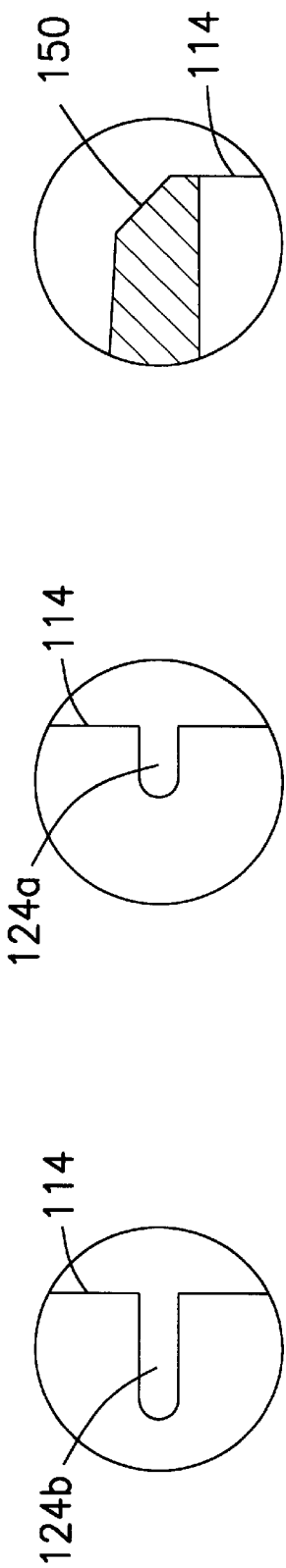
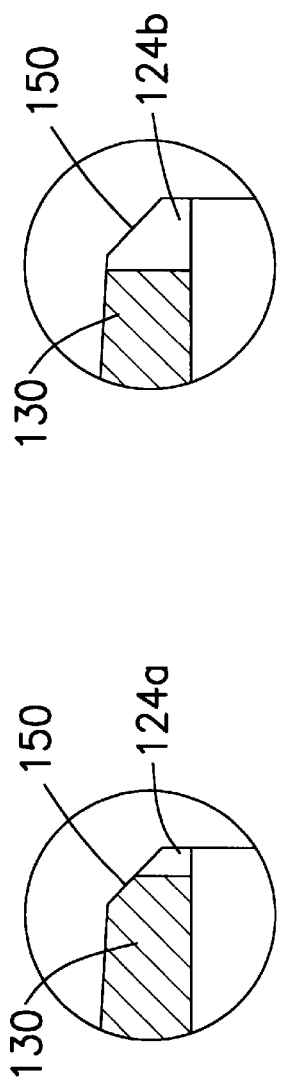

DISTAL END FOR LIGATING BAND DISPENSER

FIELD OF THE INVENTION

The present invention relates generally to the field of tissue ligation, and more particularly to an improved distal end for a device for dispensing ligating bands.

BACKGROUND INFORMATION

Physicians have used elastic ligating bands to treat lesions, including internal hemorrhoids and mucositis and for performing mechanical hemostasis. The object of such ligation is to position a ligating band, which is usually elastic, over the targeted lesion or blood vessel section by first stretching the band beyond its undeformed diameter and then drawing the tissue to be ligated within the band. Thereafter the band is released so that it contracts, applying inward pressure on the section of tissue caught within the band. The effect of the inward pressure applied by the band is to stop all circulation through the targeted tissue, thereby causing the tissue to die. The body then sloughs off the dead tissue or the dead tissue may be aspirated into an endoscope or a similar device.

Previous ligating band dispensers allowed a user to dispense only a single ligating band at a time. That is, after a single ligating band was dispensed, if a user wanted to ligate another portion of tissue, the user would remove the device from the patient's body, load a new ligating band on the device and reinsert the device to the desired area within the patient's body.

U.S. Pat. No. 5,398,844 to Zaslavsky et al. ("the Zaslavsky patent"), expressly incorporated herein by reference, describes a ligating band dispensing device including a substantially cylindrical support surface over which elastic ligating bands are stretched. The cylindrical support surface is typically attached to the distal end of an endoscope which is advanced into the body to a target area. A user then applies suction through the endoscope to draw the tissue to be ligated into the cylindrical support surface and releases a ligating band to contract around the tissue. While the device of the Zaslavsky patent allows a user to place several ligating bands at desired locations without removing the device from the patient's body to reload ligating bands, it requires multiple pull strings to deploy the ligating bands. These pull strings may interfere with each other or become tangled. In addition, as the number of ligating bands included on the distal end of these devices has been increased, the number of pull strings increases while the dispenser itself elongates. Accordingly, the field of vision from the endoscopes to which these devices are normally coupled has been correspondingly decreased.

SUMMARY OF THE INVENTION

The present invention is directed to a supporting structure for a ligating band dispensing device being adapted to be coupled to a distal end of an endoscope. The supporting structure comprises a substantially cylindrical support surface adapted to receive a plurality of ligating bands thereon, wherein the support surface includes a channel extending therethrough from a distal end to a proximal end. The supporting structure further includes a plurality of shallow slots and deeper slots disposed on the distal end for retaining a trigger string. The shallow slots and deeper slots may, for example, be arranged in an alternating fashion, and each of the slots may be, for example, narrower than the trigger string to prevent the trigger string from prematurely exiting the slots.

The support surface may also include a plurality of axially extending ridges to assist in the deployment of the ligating bands by preventing the bands from sliding along the trigger line and facilitating rolling of the bands along the support surface.

BRIEF DESCRIPTION OF THE DRAWINGS

The present invention will be more readily understood through the following detailed description, with reference to the accompanying drawings, in which:

FIG. 7 is a detailed view of a slot of the ligating dispensing device of FIG. 5.

FIG. 8 is a detailed view of a second slot of the ligating dispensing device of FIG. 5.

FIG. 9 is a detailed cross-sectional view of an embodiment of a distal end of the ligating dispensing device of FIG. 5.

FIGS. 10 and 11 are detailed cross-sectional views of the slots of FIGS. 7 and 8, respectively, taken along lines 10—10 and 11—11 of FIG. 6, respectively.

DETAILED DESCRIPTION OF THE INVENTION

Figure 1:
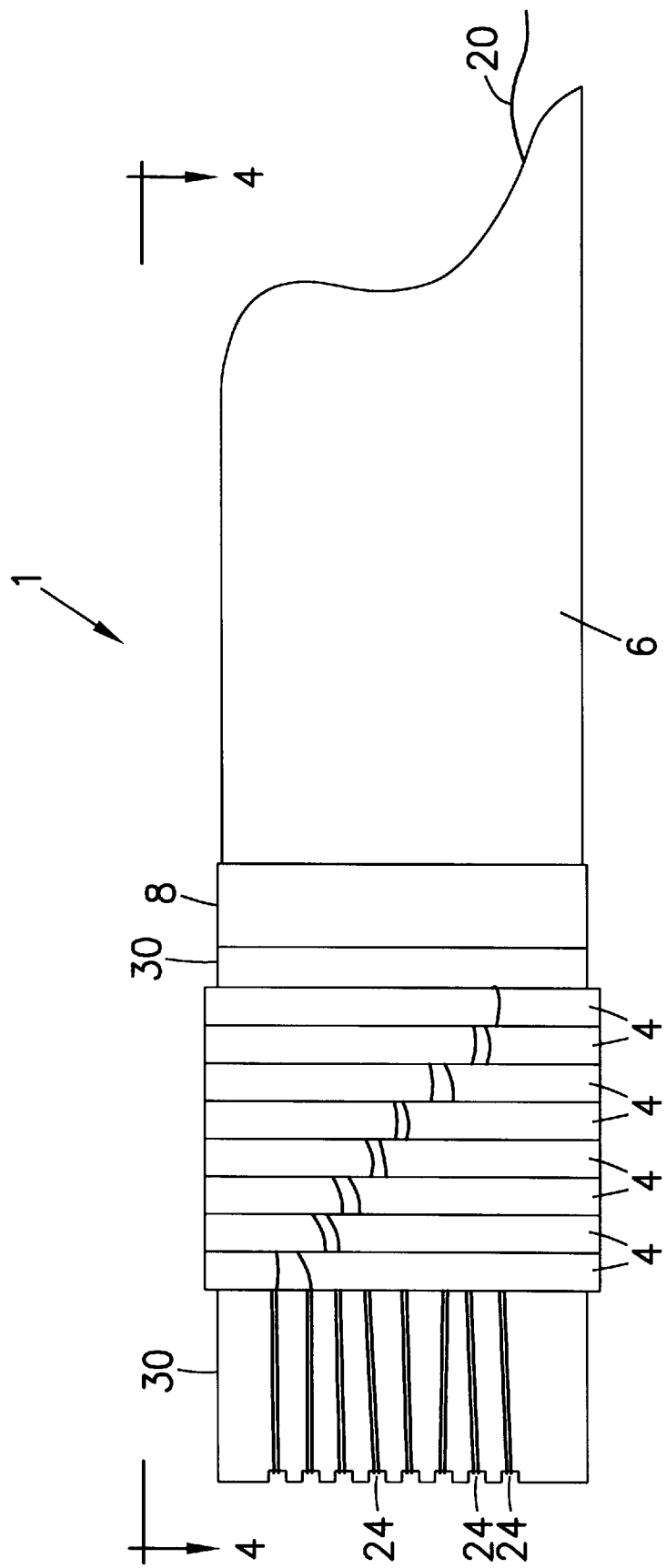
FIG. 1 is a perspective view of a distal end of a ligating band dispensing device according to a first embodiment of the present invention.
Figure 3:
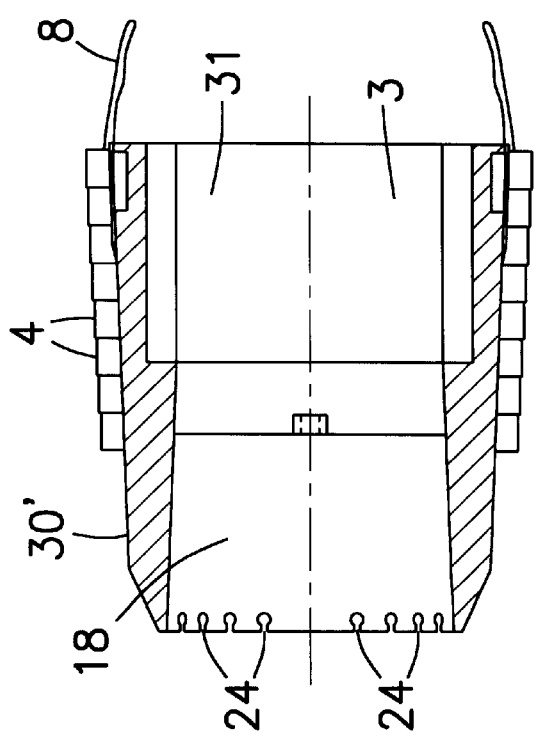
FIG. 3 is a cross-sectional view of a ligating dispensing device according to a second embodiment of the present invention.
Figure 6:
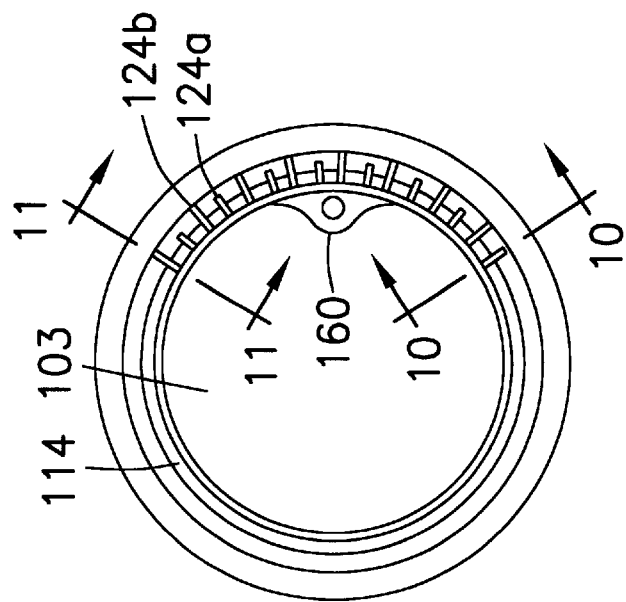
FIG. 6 is an end view of the ligating dispensing device of FIG. 5.

As illustrated in FIG. 1, a device 1 according to a first embodiment of the present invention includes a substantially cylindrical support surface 30 coupled to an elastic ring 8. A central bore 3 (not shown in FIG. 1) which extends through the support surface 30 and the elastic ring 8, in operation, receives the distal end of an endoscope 6. A plurality (8 in this case) of ligating bands 4 are received around the support surface 30 with a trigger line 20 wrapping around each of the ligating bands 4 in a repeating pattern. The support surface 30 and the support surface 30' of FIG. 3 for receiving 8 ligating bands 4 thereon will preferably be between 0.5 and 0.8 inches in length and may preferably be between 0.65 and 0.75 inches in length. While the support surface 30" of FIG. 4 may preferably be between 0.45 and 0.65 inches in length and is more preferably between 0.5 and 0.6 inches in length. Of course, those skilled in the art will understand that the length of the support surface may need to be varied depending on the thickness of the ligating bands (in a direction distal to proximal) received thereon. The ligating bands 4 of FIG. 3 are received on the support surface 30 so that a distal-most band 4 is separated from a distal end 14 of the support surface 30 by an area 15 which is, except for the trigger line 20, substantially free from visual obstructions. The support surface 30 is preferably substantially transparent. However, those skilled in the art will understand that at least the area 15, which preferably extends 0.2–0.3" should be transparent.

The trigger line 20 extends from a proximal end accessible to a user, through a lumen 22 in the endoscope 6 to pass through the central bore 3 and out to the support surface 30 via a first one of a plurality of grooves 24. The trigger line 20 then extends across the support surface 2, passes over the distal-most of the ligating bands 4 and wraps underneath this ligating band 4 to extend back into the first groove 24. The trigger line 20 then loops under the distal end 14 of the support surface 30 and passes through a second groove 24 adjacent to the first groove, passes under the distal-most band 4, wraps around this band 4 and passes under and around a second band immediately proximal to the distal-most band 4. The trigger line 20 continues over the second band 4 and passes back under the distal-most band 4 to extend to the second groove 24, returning from the second groove 24 to wrap over and around the second band 4, under the third band 4, etc. This pattern is repeated until the trigger line 20 extends around each of the ligating bands 4 received on the support surface 30. Of course, the arrangement of the trigger line 20 may be varied substantially so long as it is arranged so that a user is permitted to release each of the plurality of ligating bands 4 one at a time at each of a corresponding plurality of locations within the patient. Thus, for example, a separate trigger line 20 may be provided for each of the ligating bands 4 or a single line 20 may be divided at some point between the user and the support surface 30 into a plurality of filaments each of which is coupled to a respective ligating band 4.

The endoscope 6 extends past the juncture between the ring 8 and the support surface 30 to a shoulder 10 formed at a portion of the central bore 3 within the support surface 30. This shoulder 10 may preferably be located beneath one of the distal-most of the ligating bands 4 and is most preferably located so that, prior to releasing any ligating bands, the shoulder is beneath the third ligating band (counting distal to proximal) preferably between 0.35 and 0.5", and more preferably approximately 0.38" from the distal end of the support surface 30. This shoulder 10 prevents the endoscope 6 from moving past a distal-most position within the central bore 3, to create a substantially unobstructed space 18 extending from the distal end 14 proximally to the distal end of the endoscope 6. This space 18, which is dimensioned similarly to that of the support surface 2 described above, is separated at the shoulder 10 from an increased diameter endoscope receiving portion 31 of the bore 3 which preferably has a diameter of between 0.4 and 0.5 inches depending upon the diameter of the endoscope 6 which is to be received therein. The space 18 provides an area into which tissue to be ligated may be drawn so that a ligating band 4 released from the support surface 30 will encircle and grip the tissue to the extent necessary for the band 4 to be maintained in position on the tissue after the tissue has been released. That is, the tissue is drawn into the space 18 by known means such as, for example suction or a gripping mechanism (not shown) provided via the lumen 22. Thus, the placement of the endoscope 6 within the rigid support surface 30 and the extension of the support surface 30 distally beyond the distal-most ligating band 4 allow the space 18 to extend distally of the distal-most band 4.

Figure 2:
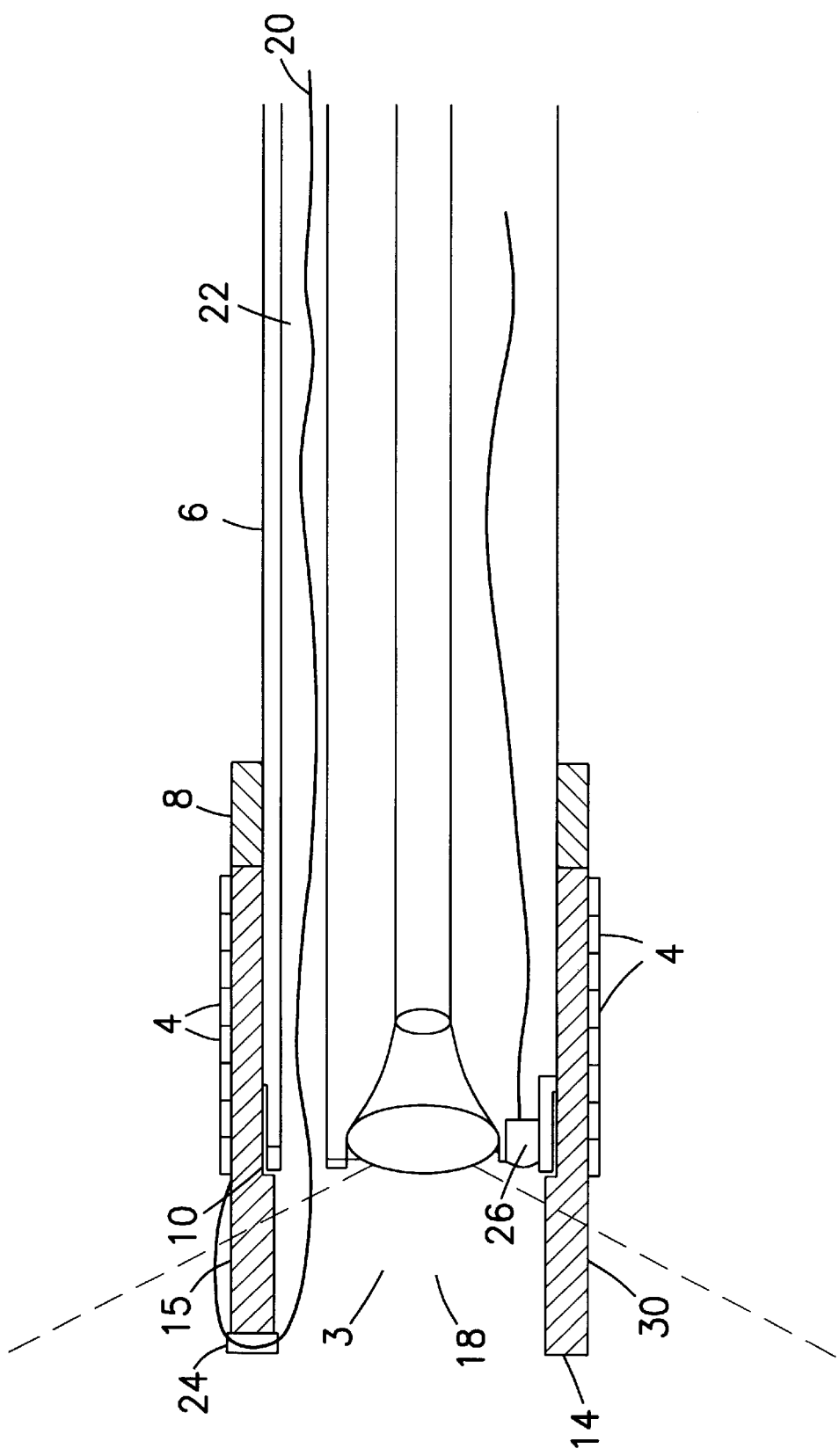
FIG. 2 is a cross-sectional view of the ligating band dispensing device of FIG. 1, taken along line 4—4 of FIG. 1.

As noted above, the distal end of the endoscope 6 includes an optical device 16 and a light source 26 which allow a user to view the area adjacent to the distal end of the device 1. The placement of the endoscope 6 within the rigid support surface 30 and the consequent placement of the tissue receiving space 18 distally toward the distal-most band 4 (or distally past all of the ligating bands 4), allows the field of vision of the optical device 16 (shown by the dotted lines in FIG. 2) to be increased relative to that obtained with an endoscope 6 seated proximal to the juncture between the ring 8 and the support surface 30. Those skilled in the art will understand that an increase of nearly 2 to 1 over prior placement positions of the endoscope may be obtained with this arrangement. Of course, this increase of the field of vision is achieved only when the support surface 30 is formed of a transparent material which may preferably be polycarbonate.

As described above, the elastic ring 8 of the support surface 30 grips the endoscope 6 to prevent if from becoming separated from the support surface 30. However, those skilled in the art will understand that in order to maintain a proper fit of the endoscope 6 within the rigid support surface 2, or to accommodate larger endoscopes 6, sizing the endoscope receiving portion 31 of the central bore 3 to correspond to the diameter of the distal end of a particular endoscope 6 will provide a more secure and stable mating with the support surface 30.

In operation, a plurality of ligating bands 4 are placed on the support surface 30 with the trigger line 20 threaded between the bands 4 as described above. Then an endoscope 6 is passed into the endoscope receiving portion 31 of the central bore 3 via an opening formed in the proximal end of the elastic ring 8 until a distal end of the endoscope 6 contacts the shoulder 10 and the trigger line 20 extended from the proximal end of the endoscope 6 through the central bore 3 to the ligating bands 4 (preferably via the lumen 22). The endoscope 6 is then inserted into a patient and advanced, under visual observation (via optical device 16) until the distal end 14 of the support surface 30 is adjacent to a portion of tissue to be ligated. The user then draws the tissue into the space 18 by, for example, advancing a gripping device (not shown) through the lumen 22 and grasping the tissue, or by applying suction through the lumen 22. When the tissue is in a desired position within the space 18, a user draws the trigger line 20 proximally through the lumen 22 until the distal-most ligating band 4 is released from the support surface 30 to ligate the tissue. As described in the Zaslavsky patent, the trigger mechanism of a ligating device incorporating a support surface according to the present invention will preferably provide the user with a tactile indication that a band 4 has been released. Additional bands may be triggered at the same site if desired using the same technique.

Thereafter, the user releases the tissue by withdrawing the gripping device or stopping application of the vacuum pressure and then visually guides the endoscope 6 to a second location within the patient. When the support surface 30 is located adjacent to a second portion of tissue to be ligated, the user repeats the process described above, releasing a second of the plurality of ligating bands 4. The second of the plurality of ligating bands 4 is preferably, after release of the first of the plurality of ligating bands 4, the distal-most ligating band 4 received on the support surface. The remaining ligating bands 4 may then be released one at a time, starting with the distal-most remaining ligating band 4 and progressing to the proximal-most band 4. Thus, the device 1 allows a user to ligate 8 or more portions of tissue without removing the device 1 from the patient while providing the user with improved control of the endoscope 6 resulting from the expanded visual field.

Figure 4:
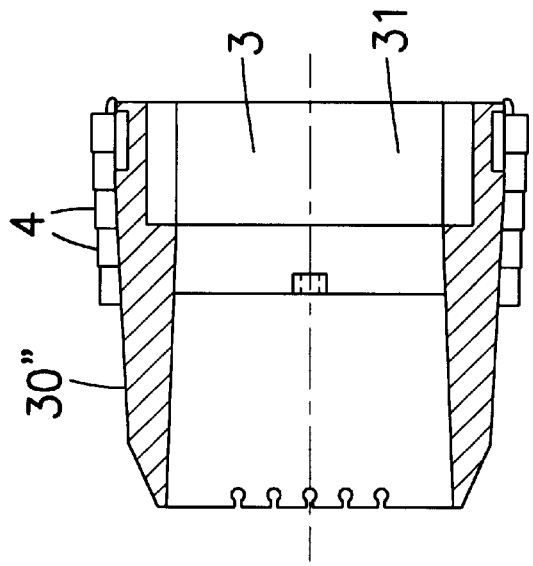
FIG. 4 is a cross-sectional view of a ligating dispensing device according to a third embodiment of the present invention.

The support surface 30'' of FIG. 4 differs from the support surfaces 30 and 30' only in that it is shorter as it is intended to receive only 5 ligating bands thereon. Of course, those skilled in the art will understand that increased numbers of ligating bands 4 may be received on a support surface as described simply by lengthening the endoscope receiving portion 31 of support surface to the extent that the increase in length of the support surface does not result in excessive irritation to the patient or to difficulties in inserting the device into a body lumen.

Figure 5:
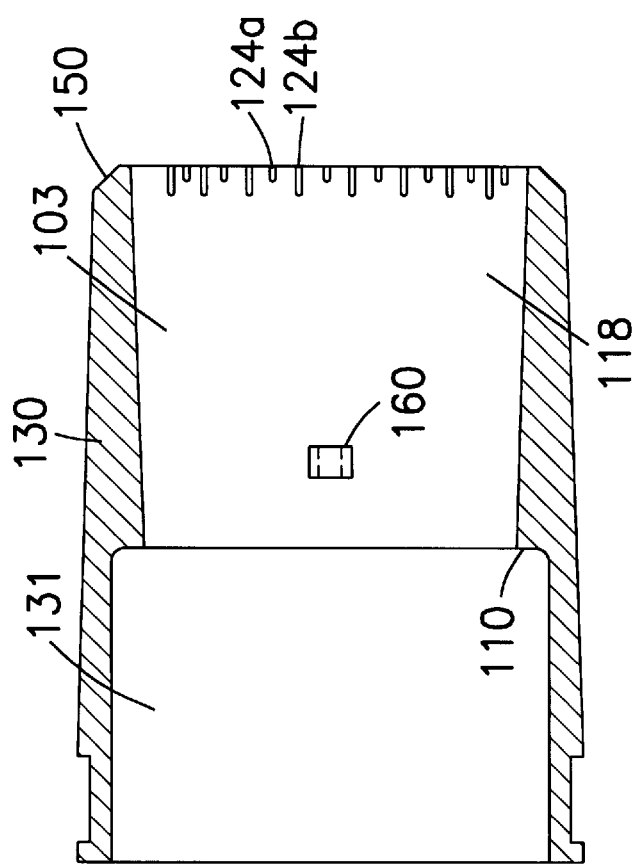
FIG. 5 is a cross-sectional view of a ligating dispensing device according to a fourth embodiment of the present invention.
Figure 12:
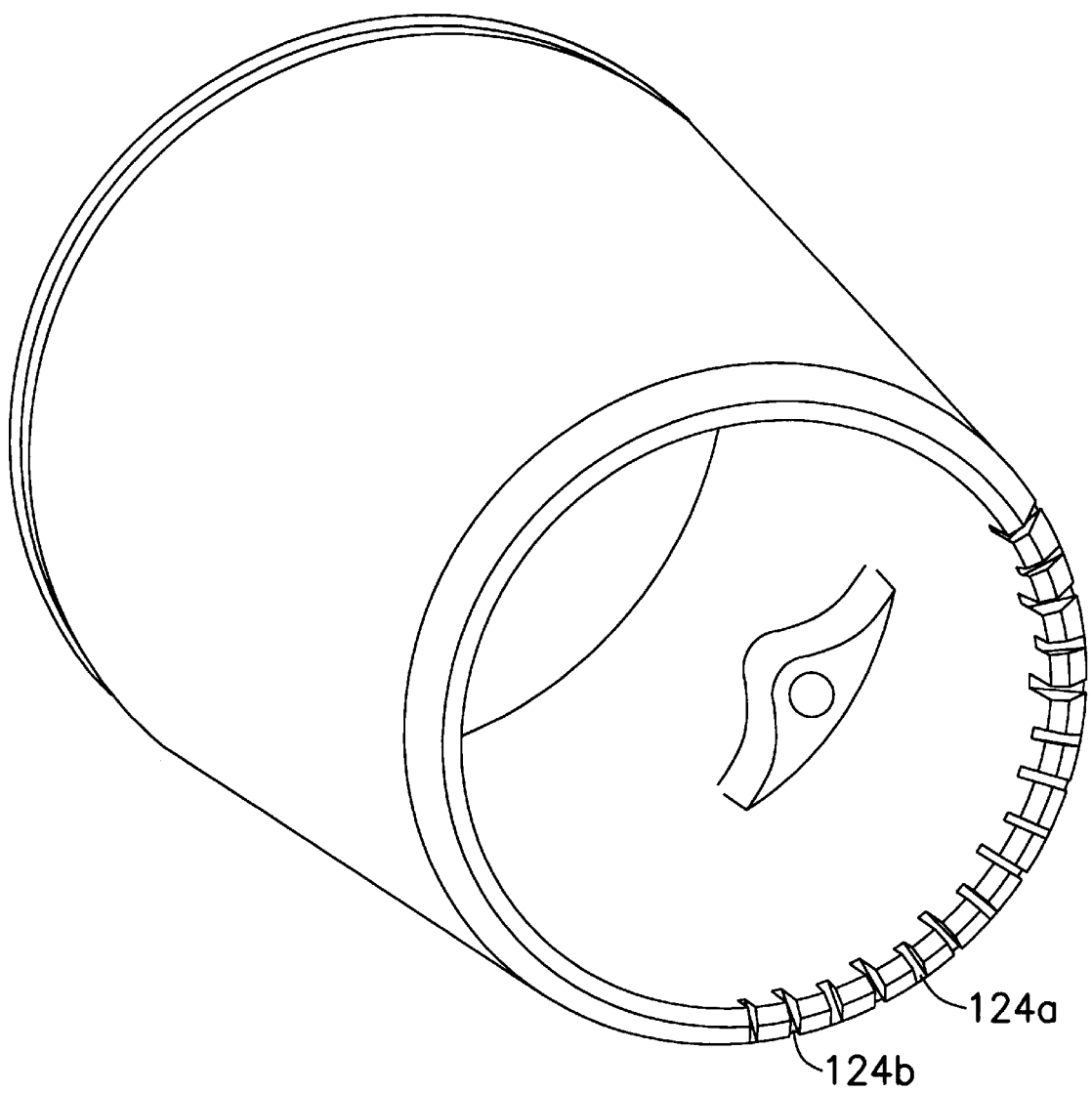
FIG. 12 is a perspective view of the ligating dispensing device of FIG. 5.

FIGS. 5–14 illustrate a fourth embodiment of the present invention. As with the above embodiments, the ligating dispenser device of FIGS. 5–12 includes a substantially cylindrical support surface 130 having a central, axially-extending bore 103 therethrough. While being substantially cylindrical, the support surface 130 may be slightly tapered in the distal direction, as shown in FIG. 5. The support surface 130 includes, for example, a shoulder 110 on its interior surface, against which an endoscope 6 may abut. An endoscope 6 place into the bore 103 will enter a proximal portion 131 of the bore 103 but will be prevented from moving further distally into a distal portion 118 of the bore 103 by the shoulder 110.

Figure 13:
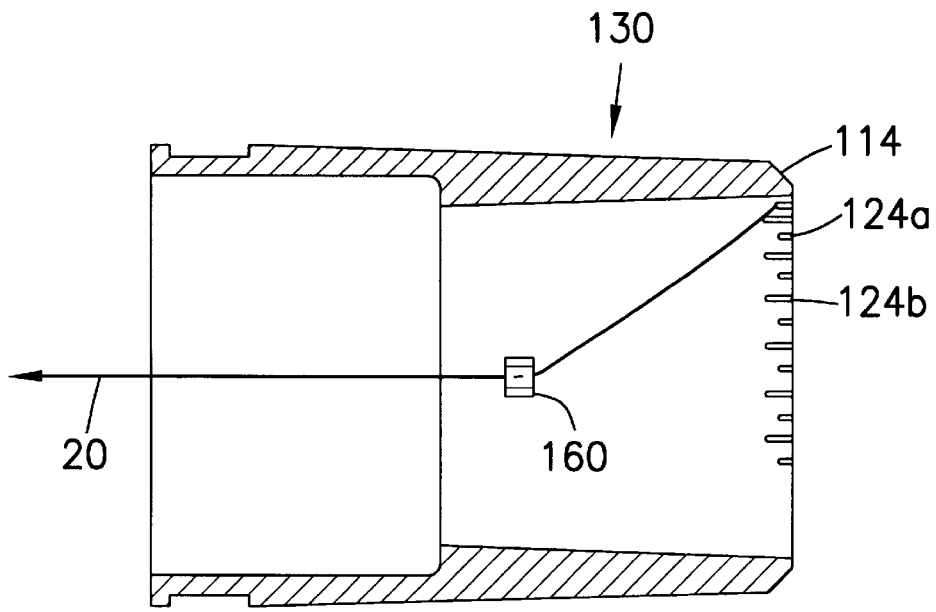
FIG. 13 is a cross-sectional view of the ligating dispenser device of FIG. 5, showing the provision of a trigger line through a ring in the device.

The support surface 130 has a distal end 114, which includes, for example, a plurality of slots 124a and 124b for receiving and retaining a trigger line 20 (not shown in FIGS. 5–12). The slots 124a are, for example, relatively shallow in depth compared to the deeper slots 124b, as shown in FIGS. 7 and 8. The slots 124a and 124b are arranged in an alternating fashion with respect to one another, so that as a trigger line 20 is looped through the slots 124a and 124b and wound around one or more bands 4, it alternatingly passes through each type of slot. In a further exemplary embodiment, the shallow slot 124a may retain the "lead string" for each band 4 (the proximal of the two segments of the trigger line 20 that together form a loop the band 4), while the deeper slot 124b may retain the "trailing string" for the band 4. A ring 160 may serve as a guide for trigger line 20 as the trigger line extends initially from the endoscope to the distal end 114 of the support surface 130, as shown in FIG. 13

In a preferred embodiment, the total number of slots 124a and 124b is equal to the number of segments of the trigger line 20 that will be retained in the slots 124a and 124b. In other words, the trigger line 20 passes, for example, through each slot 124a or 124b only once. Accordingly, a minimum number of required slots may be determined as a function of the number of bands placed on the dispenser and the number of loops of the trigger line 20 which will be wrapped around each band. For example, if the trigger line 20 passes around each band 4 once and if eight bands are present, then there could be sixteen total slots present, eight shallow slots 124a and eight deeper slots 124b. Of course, other configurations are possible. In addition, regardless of the number of segments of the trigger line 20 formed by the arrangement of the trigger line 20 and the bands 4, additional (unused) slots may be present.

Figure 14:
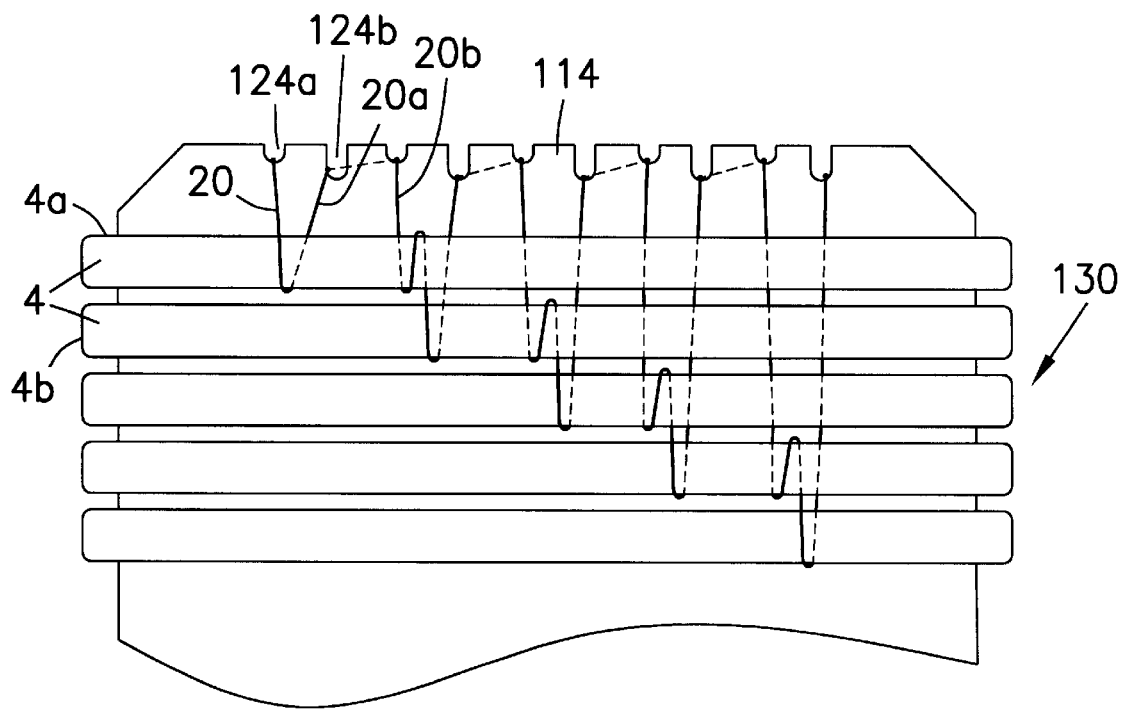
FIG. 14 is a side view of the ligating dispenser device of FIG. 5, showing an exemplary arrangement of ligating bands and trigger line.

The trigger line configuration is illustrated in FIG. 14. As can be seen, after the trigger line 20 is looped around a first one of a plurality of the bands 4, it may be extend back under the band to be looped around a second one of the bands 4. Once looped around the pair of the bands 4, the trigger line 20 may then return to the distal end 114 of the support surface 130. At the distal end 114, trigger line 20 may wind through a shallow slot 124a and a deeper slot 124b as described above, and then return proximally to loop around the second band 4 and a third of the bands 4. This configuration of the trigger line 20 allows the ligating bands 4 to be completely released from the support surface 130. For example, when the trigger line 20 in FIG. 14 pulls the distal most band 4a from the distal end 114, the trigger line loop 20a, 20b pulls through the center of the band 4a completely freeing the band 4a from the trigger line 20. The trigger line portion 20b is then positioned for the deployment of the second band 4b.

The combination of shallow slots 124a and deeper slots 124b increases deployment reliability while minimizing the possibility of the trigger line 20 prematurely leaving the slots 124a and 124b. In particular, the shallow slot 124a holds the trigger line 20 closer to the distal end 114 of the support surface 130, so that as the band 4 is pulled the trigger line 20 can draw it closer to the distal end 114, increasing deployment reliability. At the same time, the deeper slot 124b may retain the trigger line 20 further from the distal end 114, decreasing the possibility of the trigger line 20 leaving the slots. As shown in FIGS. 10 and 11, the shallow slots 124a extend, for example, only partially into a beveled portion 150 at the distal end 114 of the cylindrical housing 130, while the deeper slots 124b extend, for example, fully into the beveled portion 150. The beveled portion 150 encourages, for example, proper deployment of the bands 4 by decreasing the likelihood that a band 4 will be "stranded" at the distal end 114. A band 4 pulled onto the beveled portion 150 will tend to deploy, even without further pulling by the trigger line 20, via the elastic forces within the band 4.

In a preferred embodiment, the slots 124a and 124b are also, for example, narrower than the trigger line 20. If the width of the slots 124a and 124b is smaller than the diameter of the trigger line 20, then the trigger line 20 is more firmly retained in the slots 124a and 124b. This arrangement further minimizes the chance of the trigger line 20 coming out of the slots 124a and 124b before the associated band 4 deploys, which might leave the band 4 near the distal rim 114 of the support surface 130 and hamper the deployment of further bands 4.

In an exemplary embodiment, the support surface 130 may be approximately 0.6 to 0.8 inches in length and approximately 0.4 to 0.6 inches in outer diameter. The bore 103 may be approximately 0.3 to 0.5 inches in diameter, and the proximal portion 131 of the bore 103 may have a diameter of approximately 0.35 to 0.55 inches in diameter (so that the entire bore may include portions having diameters ranging from approximately 0.3 to 0.55 inches). The shallow slots 124a may be approximately 0.01 to 0.02 inches in depth and approximately 0.006 to 0.01 inches in width, and the deeper slots 124b may be approximately 0.02 to 0.04 inches in depth and approximately 0.006 to 0.01 inches in width. The slots 124a and 124b may be arranged around the distal end 114 with an angular spacing of approximately 6 to 10 degrees between each slot. These dimensions are exemplary and should not be construed as a limitation on the present invention.

In a further exemplary embodiment, the support surface 130 may be approximately 0.7 inches in length and approximately 0.5 inches in outer diameter. The bore 103 may be approximately 0.4 inches in diameter, and the proximal portion 131 of the bore 103 may have a diameter of approximately 0.45 inches in diameter. The shallow slots 124a may be approximately 0.015 inches in depth and approximately 0.008 inches in width, and the deeper slots 124b may be approximately 0.03 inches in depth and approximately 0.008 inches in width. The slots 124a and 124b may be arranged around the distal end 114 with an angular spacing of approximately 8 degrees between each slot. Again, these dimensions are exemplary and should not be construed as a limitation on the present invention.

Figure 15:
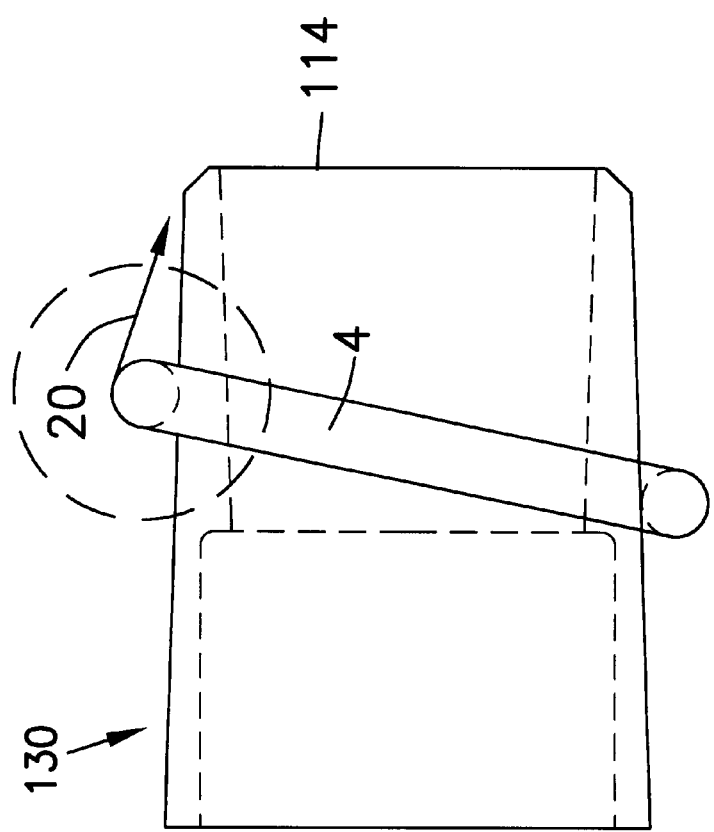
FIG. 15 is a side view of a ligating dispenser device illustrating the forces affecting movement of a ligating band.
Figure 16:
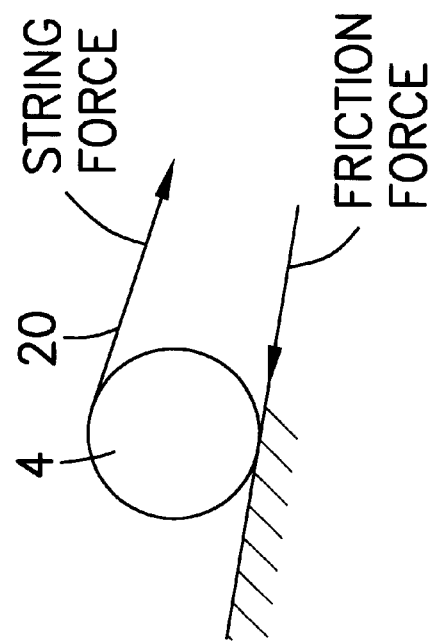
FIG. 16 is an expanded view of a highlighted portion of FIG. 15.

FIGS. 15–19 illustrate another exemplary embodiment of a support surface 130 according to the present invention. In this embodiment, the support surface 130 generally includes, for example, a plurality of raised ridges 170 to assist in the deployment of ligating bands 4. FIGS. 15 and 16 illustrate the forces involved in the deployment of a ligating band 4, FIG. 16 being an expanded view of the highlighted portion of FIG. 15. In any design in which the bands 4 are pulled towards the distal end 114 of the support surface 130, reliable band deployment is facilitated by the bands rolling rather than sliding across the support surface 130. The rolling action is caused, for example, by the trigger line 20 pulling over the top of the band 4 and by friction between the band 4 and the support surface 130. Rolling is initiated, for example, at the point in which the trigger line 20 contacts the band 4, and propagates around the band circumference. This rolling causes the band 4 to move distally.

A potential problem is created when the band 4 slides instead of rolls. If the band 4 slides across the support surface 130, it tends to push the trigger line 120 ahead of it. The trigger line 120 may then come out of one or more slots 124 in the distal rim, leaving the band 4 with no effective trigger line 120. The trigger line 120 itself often exacerbates this problem, because it provides the bands 4 with a relatively low-friction surface, increasing the chance of sliding. Also, with sliding motion, there is less of a tendency for the band 4 to move at the point of the support surface 130 opposite the trigger line 120. This is particularly true if the bands 4 undergo heating from, for example, a typical sterilization cycle.

Figure 18:
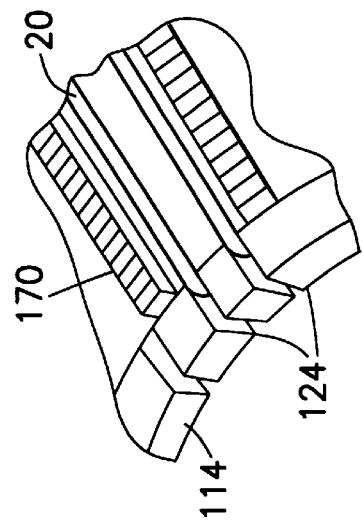
FIG. 18 is a perspective view of a portion of the ligating dispenser device of FIG. 17.
Figure 17:
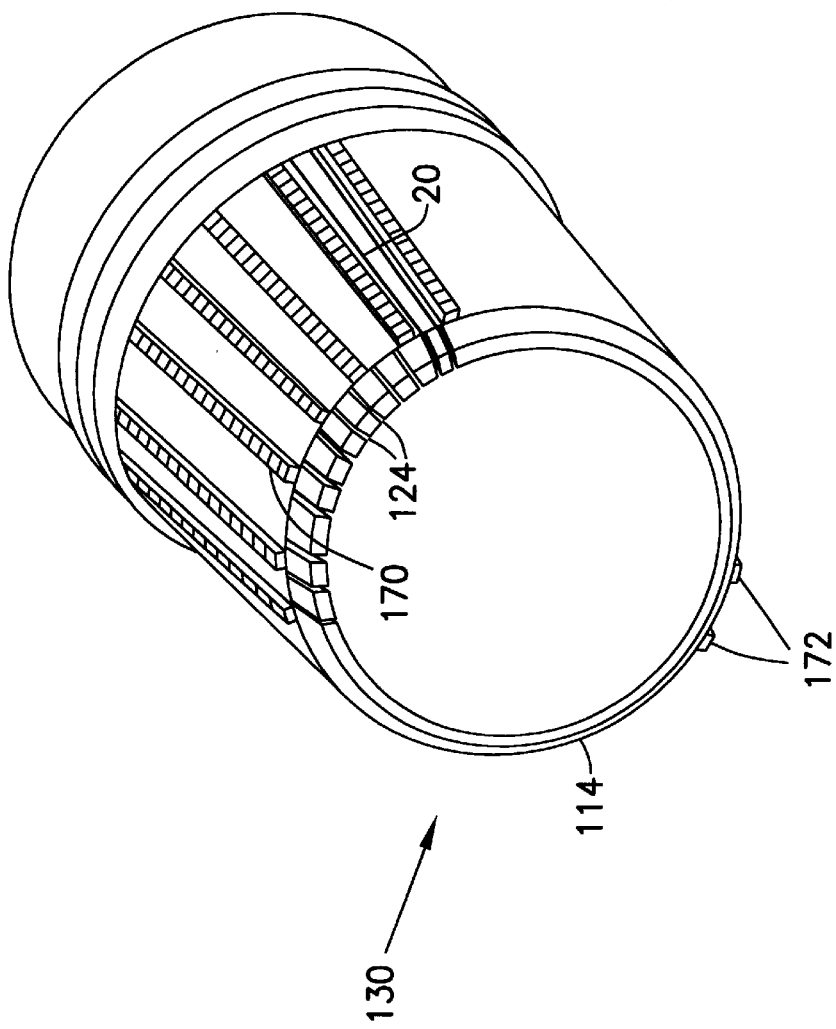
FIG. 17 is a perspective view of a further exemplary embodiment of a ligating dispenser device according to the present invention.
Figure 19:
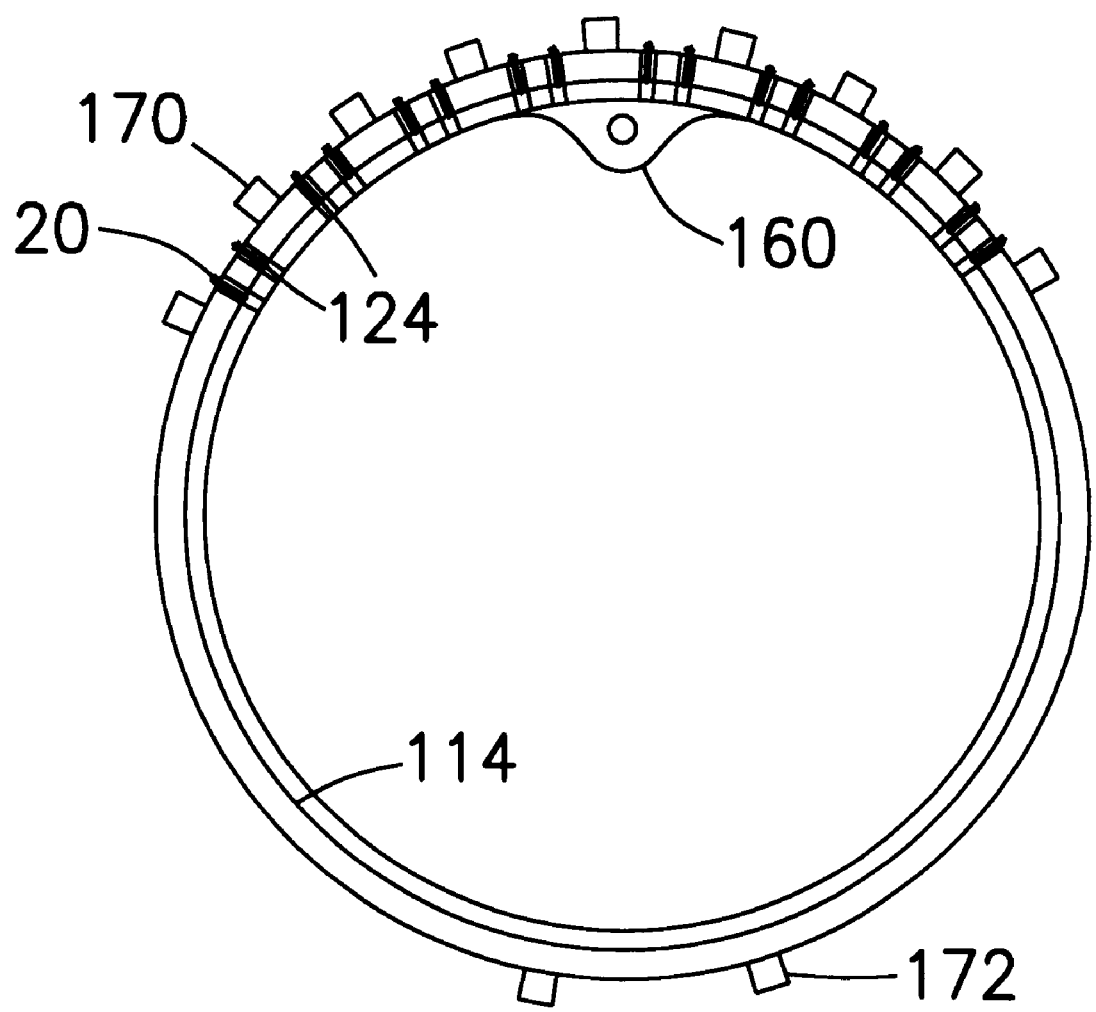
FIG. 19 is a front view of the ligating dispenser device of FIG. 17.

An exemplary embodiment of a support surface 130 according to the present invention includes, for example, a plurality of primary ridges 170 and at least one secondary ridge 172 to facilitate rolling of the bands 4. As shown in FIGS. 17–19, the primary ridges 170 may be disposed in the vicinity of the slots 124. In an exemplary arrangement, the primary ridges 170 may be arranged so that a pair of slots 124 are disposed between each adjacent pair of primary ridges 170. If the support surface 130 also includes shallow slots 124a and deeper slots 124b as described above, then one of each type of slot may be disposed, for example, between each corresponding pair of primary ridges 170.

The primary ridges 170 are preferably thick enough so that the bands 4 are maintained remote of the trigger line 20. In this manner, bands 4 are unable to slide along or push trigger line 120. In a further exemplary embodiment, the primary ridges 170 include a frictional surface on their outer face (the face contacting the bands 4). The frictional surface may include, for example, a plurality or transverse grooves or a sawtooth profile. Other friction-inducing features may also be provided in conjunction with or alternative to these exemplary features. The frictional surface increases the tendency of the bands 4 to roll rather than slide, increasing deployment reliability.

The exemplary support surface 130 also includes, for example, at least one axially extending secondary ridge 172. In the embodiment of FIGS. 17–19, for example, a pair of secondary ridges 172 are provided. Secondary ridges 172 reduce, for example, the contact area between the bands 4 and the support surface 130, thereby reducing the tendency of the bands 4 to stick to the support surface 130. In addition, secondary ridges 172 also allow lubricant, which is often applied to the support surface 130 to aid insertion into the patient, under the bands 4, further assisting propagation. The secondary ridges 172 are preferably disposed, for example, substantially diametrically opposite any primary ridges 170 (if present), meaning simply that the secondary ridges 172 are preferable disposed, in relation to the primary ridges 170, on the opposite side of the circumference of the support surface 130. This exemplary configuration is illustrated in FIGS. 17 and 19.

The support surface 130 has been described with respect to several exemplary embodiments. However, the present invention should not be limited to the particular embodiments described herein, even where particular features have not been designated as exemplary. For example, primary ridges 170 and secondary ridges 172 could be formed around the entire circumference of the support surface 130, essentially forming a series of ridges that span the circumference of the support surface 130. In addition, there are many other modifications of the disclosed embodiments which will be apparent to those of skill in the art. It is understood that these modifications are within the teaching of the present invention which is to be limited only by the claims appended hereto.

What is claimed is:

1. A supporting structure for a ligating band dispensing device, the supporting structure comprising:
   a substantially cylindrical support surface adapted to receive a plurality of ligating bands thereon, the support surface having a channel extending axially therethrough from a distal end to a proximal end, the support surface including a plurality of shallow slots and a plurality of deeper slots disposed on the distal end for retaining a trigger line.

2. The supporting structure according to claim 1, wherein the support surface has a length of approximately 0.6 to 0.8 inches and an outer diameter of approximately 0.4 to 0.6 inches, wherein the channel has a diameter of approximately 0.3 to 0.55 inches, wherein the shallow slots have a depth of approximately 0.01 to 0.02 inches and a width of approximately 0.006 to 0.01 inches, wherein the deeper slots have a depth of approximately 0.02 to 0.04 inches and a width of approximately 0.006 to 0.01 inches, and wherein the plurality of shallow slots and the plurality of deeper slots are arranged around the distal end with an angular spacing of approximately 6 to 10 degrees between each slot.

3. The supporting structure according to claim 1, wherein a width of each of the shallow slots and deeper slots is less than a diameter of the trigger line.

4. The supporting structure according to claim 3, wherein the support surface has a length of approximately 0.6 to 0.8 inches and an outer diameter of approximately 0.4 to 0.6 inches, wherein the channel has a diameter of approximately 0.3 to 0.55 inches, wherein the shallow slots have a depth of approximately 0.01 to 0.02 inches and a width of approximately 0.006 to 0.01 inches, wherein the deeper slots have a depth of approximately 0.02 to 0.04 inches and a width of approximately 0.006 to 0.01 inches, and wherein the plurality of shallow slots and the plurality of deeper slots are arranged around the distal end with an angular spacing of approximately 6 to 10 degrees between each slot.

5. The supporting structure according to claim 1, wherein the plurality of shallow slots and the plurality of deeper slots are arranged in an alternating fashion.

6. The supporting structure according to claim 5, wherein the support surface has a length of approximately 0.6 to 0.8 inches and an outer diameter of approximately 0.4 to 0.6 inches, wherein the channel has a diameter of approximately 0.3 to 0.55 inches, wherein the shallow slots have a depth of approximately 0.01 to 0.02 inches and a width of approximately 0.006 to 0.01 inches, wherein the deeper slots have a depth of approximately 0.02 to 0.04 inches and a width of approximately 0.006 to 0.01 inches, and wherein the plurality of shallow slots and the plurality of deeper slots are arranged around the distal end with an angular spacing of approximately 6 to 10 degrees between each slot.

7. The supporting structure according to claim 5, wherein a width of each of the shallow slots and deeper slots is less than a diameter of the trigger line.

8. The supporting structure according to claim 7, wherein the support surface has a length of approximately 0.6 to 0.8 inches and an outer diameter of approximately 0.4 to 0.6 inches, wherein the channel has a diameter of approximately 0.3 to 0.55 inches, wherein the shallow slots have a depth of approximately 0.01 to 0.02 inches and a width of approximately 0.006 to 0.01 inches, wherein the deeper slots have a depth of approximately 0.02 to 0.04 inches and a width of approximately 0.006 to 0.01 inches, and wherein the plurality of shallow slots and the plurality of deeper slots are arranged around the distal end with an angular spacing of approximately 6 to 10 degrees between each slot.

9. The supporting structure according to claim 1, wherein the support surface includes a total number of the shallow slots and the deeper slots so that, when the ligating bands and the trigger line are arranged on the support surface, the trigger line passes through each slot at most once.

10. The supporting structure according to claim 9, wherein the support surface has a length of approximately 0.6 to 0.8 inches and an outer diameter of approximately 0.4 to 0.6 inches, wherein the channel has a diameter of approximately 0.3 to 0.55 inches, wherein the shallow slots have a depth of approximately 0.01 to 0.02 inches and a width of approximately 0.006 to 0.01 inches, wherein the deeper slots have a depth of approximately 0.02 to 0.04 inches and a width of approximately 0.006 to 0.01 inches, and wherein the plurality of shallow slots and the plurality of deeper slots are arranged around the distal end with an angular spacing of approximately 6 to 10 degrees between each slot.

11. The supporting structure according to claim 9, wherein a width of each of the shallow slots and deeper slots is less than a diameter of the trigger line.

12. The supporting structure according to claim 11, wherein the support surface has a length of approximately 0.6 to 0.8 inches and an outer diameter of approximately 0.4 to 0.6 inches, wherein the channel has a diameter of approximately 0.3 to 0.55 inches, wherein the shallow slots have a depth of approximately 0.01 to 0.02 inches and a width of approximately 0.006 to 0.01 inches, wherein the deeper slots have a depth of approximately 0.02 to 0.04 inches and a width of approximately 0.006 to 0.01 inches, and wherein the plurality of shallow slots and the plurality of deeper slots are arranged around the distal end with an angular spacing of approximately 6 to 10 degrees between each slot.

13. The supporting structure according to claim 9, wherein the plurality of shallow slots and the plurality of deeper slots are arranged in an alternating fashion.

14. The supporting structure according to claim 13, wherein the support surface has a length of approximately 0.6 to 0.8 inches and an outer diameter of approximately 0.4 to 0.6 inches, wherein the channel has a diameter of approximately 0.3 to 0.55 inches, wherein the shallow slots have a depth of approximately 0.01 to 0.02 inches and a width of approximately 0.006 to 0.01 inches, wherein the deeper slots have a depth of approximately 0.02 to 0.04 inches and a width of approximately 0.006 to 0.01 inches, and wherein the plurality of shallow slots and the plurality of deeper slots are arranged around the distal end with an angular spacing of approximately 6 to 10 degrees between each slot.

15. The supporting structure according to claim 13, wherein a width of each of the shallow slots and deeper slots is less than a diameter of the trigger line.

16. The supporting structure according to claim 15, wherein the support surface has a length of approximately 0.6 to 0.8 inches and an outer diameter of approximately 0.4 to 0.6 inches, wherein the channel has a diameter of approximately 0.3 to 0.55 inches, wherein the shallow slots have a depth of approximately 0.01 to 0.02 inches and a width of approximately 0.006 to 0.01 inches, wherein the deeper slots have a depth of approximately 0.02 to 0.04 inches and a width of approximately 0.006 to 0.01 inches, and wherein the plurality of shallow slots and the plurality of deeper slots are arranged around the distal end with an angular spacing of approximately 6 to 10 degrees between each slot.

17. A supporting structure for a ligating band dispensing device, the supporting structure comprising:
   a substantially cylindrical support surface adapted to receive a plurality of ligating bands and a trigger line on an outer surface thereof, the support surface having a channel extending axially therethrough from a distal end to a proximal end, the support surface including a plurality of axially extending primary ridges disposed on the outer surface, the primary ridges maintaining the plurality of ligating bands in a position remote from the trigger line.

18. The supporting structure according to claim 17, wherein each of the plurality of primary ridges includes a frictional surface on an outer face.

19. The supporting structure according to claim 18, wherein the frictional surface includes a plurality of transverse grooves.

20. The supporting structure according to claim 18, wherein the frictional surface includes a sawtooth profile.

21. The supporting structure according to claim 17, wherein the support surface further includes a plurality of shallow slots and a plurality of deeper slots disposed on the distal end for retaining the trigger line.

22. The supporting structure according to claim 21, wherein a width of each of the shallow slots and deeper slots is less than a diameter of the trigger line.

23. The supporting structure according to claim 21, wherein the plurality of shallow slots and the plurality of deeper slots are arranged in an alternating fashion.

24. The supporting structure according to claim 23, wherein a width of each of the shallow slots and deeper slots is less than a diameter of the trigger line.

25. The supporting structure according to claim 21, wherein the support surface includes a total number of the shallow slots and the deeper slots so that, when the ligating bands and the trigger line are arranged on the support surface, the trigger line passes through each slot at most once.

26. The supporting structure according to claim 25, wherein a width of each of the shallow slots and deeper slots is less than a diameter of the trigger line.

27. The supporting structure according to claim 25, wherein the plurality of shallow slots and the plurality of deeper slots are arranged in an alternating fashion.

28. The supporting structure according to claim 27, wherein a width of each of the shallow slots and deeper slots is less than a diameter of the trigger line.

29. The supporting structure according to claim 28, wherein the support surface has a length of approximately 0.6 to 0.8 inches and an outer diameter of approximately 0.4 to 0.6 inches, wherein the channel has a diameter of approximately 0.3 to 0.55 inches, wherein the shallow slots have a depth of approximately 0.01 to 0.02 inches and a width of approximately 0.006 to 0.01 inches, wherein the deeper slots have a depth of approximately 0.02 to 0.04 inches and a width of approximately 0.006 to 0.01 inches, and wherein the plurality of shallow slots and the plurality of deeper slots are arranged around the distal end with an angular spacing of approximately 6 to 10 degrees between each slot.

30. The supporting structure according to claim 28, wherein the plurality of shallow slots and deeper slots are grouped in slot pairs, each of the slot pairs including one of the shallow slots and an adjacent one of the deeper slots, and wherein each of the slot pairs is disposed between a corresponding pair of the primary ridges.

31. The supporting structure according to claim 17, the outer surface of the support surface further including at least one axially extending secondary ridge, the at least one secondary ridge maintaining the ligating bands remote from the support surface.

32. The supporting structure according to claim 31, wherein the at least one secondary ridge includes a plurality of secondary ridges, the plurality of secondary ridges disposed substantially diametrically opposite the plurality of primary ridges.

33. The supporting structure according to claim 32, wherein each of the plurality of primary ridges includes a frictional surface on an outer face.

34. The supporting structure according to claim 33, wherein the frictional surface includes a plurality of transverse grooves.

35. The supporting structure according to claim 33, wherein the frictional surface includes a sawtooth profile.

36. The supporting structure according to claim 31, wherein the support surface further includes a plurality of shallow slots and a plurality of deeper slots disposed on the distal end for retaining the trigger line.

37. The supporting structure according to claim 36, wherein the plurality of shallow slots and the plurality of deeper slots are arranged in an alternating fashion.

38. The supporting structure according to claim 37, wherein the support surface includes a total number of the shallow slots and the deeper slots so that, when the ligating bands and the trigger line are arranged on the support surface, the trigger line passes through each slot at most once.

39. The supporting structure according to claim 38, wherein a width of each of the shallow slots and deeper slots is less than a diameter of the trigger line.

40. The supporting structure according to claim 39, wherein the support surface has a length of approximately 0.6 to 0.8 inches and an outer diameter of approximately 0.4 to 0.6 inches, wherein the channel has a diameter of approximately 0.3 to 0.55 inches, wherein the shallow slots have a depth of approximately 0.01 to 0.02 inches and a width of approximately 0.006 to 0.01 inches, wherein the deeper slots have a depth of approximately 0.02 to 0.04 inches and a width of approximately 0.006 to 0.01 inches, and wherein the plurality of shallow slots and the plurality of deeper slots are arranged around the distal end with an angular spacing of approximately 6 to 10 degrees between each slot.

41. The supporting structure according to claim 40, wherein the plurality of shallow slots and deeper slots are grouped in slot pairs, each of the slot pairs including one of the shallow slots and an adjacent one of the deeper slots, and wherein each of the slot pairs is disposed between a corresponding pair of the primary ridges.

\* \* \* \* \*